United States Patent [19]
Schenkel et al.

[11] Patent Number: 4,650,676
[45] Date of Patent: Mar. 17, 1987

[54] ANTIGENS AND MONOCLONAL ANTIBODIES REACTIVE AGAINST MEROZOITES OF EIMERIA SPP.

[75] Inventors: Robert H. Schenkel, Yardley, Pa.; Pallaiah Thammana, Hazlet; Rosie B. Wong, Piscataway, both of N.J.

[73] Assignee: American Cyanamid Company, Stamford, Conn.

[21] Appl. No.: 591,289

[22] Filed: Mar. 19, 1984

Related U.S. Application Data

[63] Continuation-in-part of Ser. No. 524,953, Aug. 19, 1983, abandoned.

[51] Int. Cl.[4] ............................................. A61K 39/012
[52] U.S. Cl. ........................................ 424/88; 424/92; 435/947
[58] Field of Search ....................... 260/112 R, 112 B; 435/68, 947, 948; 424/85, 88

[56] References Cited

U.S. PATENT DOCUMENTS 3,147,186 4/1961 Edgar ..................................... 424/88
4,438,097 3/1984 Shirley ................................... 424/88

OTHER PUBLICATIONS

Onaga et al, Leukocyte Migration Inhibition in Chicken Immunized by *E. Tenella,* Immunology, Parasitological, 71(7), Biol. Abst. #45672.
Bedrnik et al, An Antigen from *E. Tenella* Merozoite . . . , Immunology, Parasitological, Biological Abst. #64909.
Danforth, *J. Parasitol,* 68(3), 1982, pp. 392–397, Development of Hybridoma–Produced Antibodies Directed Against *E. Tenella* and *E. Mitis.*
Speer et al, *J. Parasitol,* 69(4), 1983, pp. 775–777.
Speer et al, *J. Protozool,* 30(3), 1983, pp. 548–554.

*Primary Examiner*—Morton Foelak
*Assistant Examiner*—Garnette D. Draper
*Attorney, Agent, or Firm*—Estelle J. Tsevdos

[57] ABSTRACT

Monoclonal antibodies against merozoites and sporozoites of *Eimeria tenella* are obtained by use of hybridoma technology. Specific antigens for use as vaccines in the prevention and treatment of coccidiosis and hybridoma cultures producing monoclonal antibodies are described.

10 Claims, No Drawings

ANTIGENS AND MONOCLONAL ANTIBODIES REACTIVE AGAINST MEROZOITES OF EIMERIA SPP.

This application is a continuation-in-part of application Ser. No. 524,953, filed 8-19-83, now abandoned.

The invention herein described relates to obtaining of monoclonal antibodies which react specifically against merozoites and sporozoites of the parasite *Eimeria tenella*. Such antibodies are obtained by means of hybridoma technology. Hybridoma cultures producing antibodies against *E. tenella* are described. Merozoite antigens are identified and characterized. These antigens, along with certain monoclonal antibodies, are effective for the prevention and treatment of coccidiosis. The antigens of the invention are useful as vaccines against coccidiosis.

By way of background, coccidiosis is a disease of animals caused by a variety of protozoan parasites. Avian coccidiosis is a devastating disease of poultry caused by a variety of species of the genus Eimeria. This disease has a complicated life cycle consisting of both asexual and sexual stages. Chickens are initially infected with the disease after ingestion of free-living oocysts which are generally associated with fecal material. Oocysts develop into invasive asexual sporozoites in the chicken's digestive tract. The sporozoites infect epthelial cells and develop into multinucleate structures known as schizonts. Each schizont matures and eventually liberates multiple invasive asexual structures known as merozoites. These merozoites leave the infected cell and reinvade other epithelial cells. The multiple invasive asexual stages involving sporozoites and merozoites account for much of the pathology of coccidiosis. The sexual cycle of coccidiosis is initiated when merozoites differentiate into gametocytes. Fertilization occurs and the fertilization products known as oocysts are released in the feces. Thus the parasite's life cycle is completed. In chickens, the life cycle of *Eimeria tenella*, a representative species, is completed in about seven to nine days.

Due to the tremendous economic losses inflicted on the poultry industry by Eimeria species, a vaccine against the parasite is highly desirable. However, due to the complexity of the life cycle of the parasite and the variability of the quantity of antigens present in each stage, it has been observed that deactivated or killed parasites have not generated consistent immunity in the past. One solution to this problem is to isolate and characterize particular antigens from the parasite and administer them in a sufficient amount to serve as an immunizing agent. Preferably such antigens will offer protection against infection by all important species. It is known that various species of Eimeria, as well as different stages in the life cycle of the same species, have both common and specific antigens [Cerna, Z, Folia Parasitologica (Prague) 17:135–140 (1970); Davis et al., Immunol. 34: 879–888 (1978); Rose, M. E., Immunol. 2: 112–122 (1959); Rose et al., Immunol. 5: 79–92 (1962); and Tanielian et al., Acta Parasitol. Yugosl. 7: 79–84 (1976)]. It is also known that development of immunity to Eimeria is species specific and in some species of domestic fowl there is significant strain-specific immunity [Jeffers, T. K.; In Long, P. L. et al. (eds.), Avian Coccidiosis, pp. 57–125, Proc. 13th Poultry Sci. Symp. (1978); Joyner, L. P., Parasitol. 59: 725–732 (1969); Long, P. L., Parasitol. 69: 337–347 (1974); and Long et al., Parasitol. 79: 451–457 (1979)]. Currently immunogens of Eimeria species capable of stimulating protective immunity in avian or mammalian hosts have not yet been isolated or identified. Such Eimeria immunogens will likely provide successful immunization against coccidiosis.

The development of lymphocyte hybridoma technology provides a tool for producing relatively large amounts of specific antibodies against various antigens of Eimeria. By fusing specific antibody-producing cells (spleen cells) with cells of a myeloma tumor, it is possible to produce hybridoma cells that secrete monoclonal antibodies directed specifically against the original sensitizing antigen (Köhler & Milstein, Nature (London) 256: 495–497 (1975)]. If monoclonal antibodies against the parasite are obtained, it may be possible to provide such antibodies to infected or susceptible fowl and to thus provide the host organism with a measure of passive immunity. Once such hybridoma cultures producing monoclonal antibodies are obtained, it is possible by various procedures to utilize such antibodies to isolate and identify specific antigens which could in turn be utilized as a vaccine to provide host organisms with a system of active immunity. Various patents concerning hybridoma cultures and monoclonal antibodies are known (i.e., U.S. Pat. Nos. 4,172,124; 4,196,265; 4,271,145; 4,361,549; 4,631,550; 4,364,932; 4,364,933; 4,364,934; 4,364,935; 4,364,936; 4,381,292; and 4,381,295).

In light of the foregoing discussion of the economic effects of coccidiosis in the area of animal husbandry and more specifically in the poultry industry, control of the protozoan parasite is highly desirable. Accordingly, an object of this invention is to provide new and useful monoclonal antibodies obtained against merozoites of the parasite *E. tenella*. A further object is to isolate and identify specific antigens of *E. tenella* useful as a vaccine for the control of avian coccidiosis. These objects are manifest in the following description and particularly delineated in the appended claims.

*Eimeria tenella*, the species which infects the caeca of chickens, is a particularly devastating parasite that causes severe bloody lesions in infected animals. *E. tenella* has two merozoite stages in its life cycle which are respectively designated as first and second generation merozoites. Immunity to *E. tenella* is known to develop during the asexual merozoite stages of its life cycle [Long, P. (ed.), *The Biology of the Coccidia*, University Park Press, Baltimore, Md. (1982)].

A preparation of *E. tenella* merozoites is used to immunize mice in order to eventually generate monoclonal antibodies following the procedure described below. The monoclonal antibodies are used to identify antigens of the parasite. Monoclonal antibodies are further evaluated to assess their ability to neutralize the growth of the parasite in vivo. Antigens which elicit monoclonal antibodies which react with at least one species of Eimeria or with either merozoites or sporozoites, and show neutralization of parasite growth, are considered protective antigens. Protective antigens are regarded as potential candidates for the development of a vaccine against avian coccidiosis.

The following non-limiting Examples further serve to illustrate the invention.

EXAMPLE 1

Quantitative Radioimmunoassay

In order to evaluate the quality of antibodies, a quantitative radioimmunoassay was developed. Glutaraldehyde-fixed sporozoites or merozoites (usually $2-5\times10^5$/ well) are centrifuged onto 96 well polyvinyl chloride or Removawell ® plates (Dynatech) at 1400x g for 10 minutes in order to attach the organism to the bottom of the wells. Sporozoites or merozoites adhering to the bottom of the plate are reacted with serum samples of mice immunized with the parasite or monoclonal antibody in culture supernatant of hybridomas. Incubation with the antibody was for 16 to 18 hours at 4° C. or for two hours at room temperature. The bound antibody was detected with a radioactively-labelled second antibody 187.1, which is a rat monoclonal antibody specific to mouse k light chain. The anti-mouse k light chain antibody is biosynthetically labelled with $^{35}$S-methionine [Yelton, D. E., et al., Hybridoma, 1: 5–11 (1982)]. The radioactivity is monitored by liquid scinitillation counting. The radioimmunoassay method is subsequently applied to the surface membranes obtained from E. tenella sporozoites to ensure the reactivity of antibodies in immune mouse sera with membrane proteins.

EXAMPLE 2

Construction of Hybridoma Cultures

Primary cultures of chicken kidney cells are infected with freshly excysted sporozoites following procedures known to the art. Merozoites released into the medium five days after infection are harvested by centrifugation at 350x g for 10 minutes. Eighteen-week-old female BALB/c mice are immunized intra-peritoneally (i.p.) with $1\times10^7$ intact or fragmented E. tenella merozoites in complete Freund's adjuvant. The animals are boosted with two i.p. injections of merozoites in medium 199 (Gibco) at two five-week intervals after initial immunization. The serum obtained three days after each boost was checked for the presence of antibodies against E. tenella merozoites by indirect immunofluorescence assay (IFA) and radioimmunoassay (RIA). Both of these assays are performed on glutaraldehyde-fixed parasites.

Hybridomas are derived following established methodology [Kwan et al. (1980), Genetic Engineering ed. by J. K. Setlow & A. Hollander, Plenum Publishing Corp., New York, pp. 31–96]. Spleen cells from two mice immunized with E. tenella merozoites are fused with a non-secreting clone of P3 myeloma, P3-x63.Ag8.653 in the presence of 30% polyethylene glycol (PEG 1000 from Baker Chemical) for eight minutes. Fused cells are distributed into 96-well tissue culture dishes (Linbro) and maintained in HAT selection medium [Littlefield, J. W., Science, 145: 709–710 (1964)]. The HAT medium is prepared in Dulbecco's modified Eagle's medium containing 20% fetal calf serum (Gibco) and 10% NCTC 109 (Microbiological Associates). Hybrids are cultured in an incubator at 37° C. and 10% $CO_2$.

Cultures are periodically assayed for the presence of antibody reactive with E. tenella merozoites by IFA and RIA methods. Positive cultures are shifted to 24 well tissue culture dishes in a medium devoid of hypoxanthine, aminopterin and thymidine. Hybridomas are cloned in soft agarose over a rat embryo fibroblast feeder layer [Coffins et al., J. Cell Phyisol., 79: 429–440 (1972)]. Positive hybridoma clones are designated by a subclone number (i.e., a clone 15.84.4 is a subclone #4 of a hybridoma designated as 15.84). The class and subclass of immunoglobulin secreted by well characterized subclones are determined by an agar double diffusion method. Detergent (NP-40) soluble extracts of hybridomas are used with rabbit-anti mouse antibody reagents (Meloy).

EXAMPLE 3

Characterization of Anti-Merozoite Monoclonal Antibodies

The characteristics of eight anti-merozoite monoclonal antibodies are presented in Table I. The majority of the monoclonal antibodies reacted with merozoites as well as sporozoites by IFA as well as RIA. Monoclonal antibodies 1.90 and 4.76 did not react with sporozoites in IFA and on occasion in RIA (see * in Table I). Monoclonal antibody 15.84 did not react with merozoites in IFA but reacted equally well with sporozoites as well as merozoites in RIA. The data summarized in Table I indicate that all the monoclonal antibodies derived from the anti-merozoite fusion are cross-reactive with sporozoites as well as merozoites of E. tenella.

TABLE I

CHARACTERIZATION OF ANTI-MEROZOITE MONOCLONAL ANTIBODIES

| Monoclonal Antibody | Specificity | | | |
|---|---|---|---|---|
| | IFA | | RIA | |
| | Mero | Sporo | Mero | Sporo |
| M1 (1.90) | + | − | + | * |
| M2 (4.76) | + | − | + | * |
| M3 (2.03) | + | + | + | + |
| M4 (13.90) | + | + | + | + |
| M5 (10.08) | + | + | + | + |
| M6 (10.84) | + | + | + | + |
| M7 (8.03) | + | + | + | + |
| M8 (15.84) | − | + | + | + |

EXAMPLE 4

Reactivity of Anti-Merozoite Monoclonal Antibodies Against Sporozoites of Different Species The monoclonal antibodies are assayed by IFA against sporozoites derived from five avian parasitic coccidia species of commercial importance. Data from these experiments are presented in Table II. Six monoclonal antibodies which reacted in IFA with sporozoites derived from E. tenella are used to study the species cross reactivity. The results demonstrate that five monoclonal antibodies cross-reacted with sporozoites derived from E. necatrix and E. maxima, and one monoclonal antibody (15.84) reacted with all five species of Eimeria tested.

TABLE II

REACTIVITY OF ANTI-MEROZOITE MONOCLONALS AGAINST SPOROZOITES OF DIFFERENT SPECIES

| Monoclonal Antibody | E. tenella | E. necatrix | E. acervulina | E. maxima | E. brunetti |
|---|---|---|---|---|---|
| M3 (2.03) | + | + | − | + | − |
| M4 (13.90) | + | + | − | + | − |
| M5 (10.08) | + | + | − | + | − |
| M6 (10.84) | + | + | − | +/− | − |
| M7 (8.03) | + | + | − | + | − |
| M8 (15.84) | + | + | + | + | + |

EXAMPLE 5

In Vivo Neutralization Assay

An in vivo procedure for assaying monoclonal antibodies is utilized to evaluate the monoclonal antibodies. Three monoclonal antibodies that react with E. tenella sporozoites are assessed by this assay. Freshly isolated sporozoites are incubated under sterile conditions with heat inactivated ascites fluid derived from three different hybridomas. The incubation period is for one hour at room temperature. The sporozoites are then introduced into the ceca of three-week-old chickens by surgical procedures. Parasite development is allowed to occur for five days after inoculation. At the end of this period, lesions are scored to evaluate the extent of the infection. The results of these experiments are expressed as percent protection offered by the monoclonal antibody and are presented in Table III. These data indicate that each antibody is at least partially protective under some conditions of this test system.

TABLE III

IN VIVO NEUTRALIZATION ASSAY WITH E. TENELLA SPOROZOITES AND ANTI-MEROZOITE MONOCLONALS

| Treatment | Number of Animals | % Protection None | Partial | Complete |
|---|---|---|---|---|
| I. Light infection (200 sporozoites/ animal) | | | | |
| Control | 14 | | 65 | 35 |
| M6 (10.84) | 13 | | 15 | 85 |
| M8 (15.84) | 18 | 5 | 17 | 78 |
| II. Heavy infection (1000 sporozoites/ animal) | | | | |
| Control | 7 | 100 | | |
| M4 (13.90) | 9 | 89 | | 11 |
| M6 (10.84) | 8 | 75 | 25 | |
| M8 (15.84) | 9 | 33 | 44 | 23 |
| III. Heavy Infection (3000 sporozoites/ animal) | | | | |
| Control | 7 | 100 | | |
| M6 (10.84) | 7 | 86 | | 14 |
| M8 (15.84) | 4 | 100 | | |

EXAMPLE 6

Antigen Characterization

E. tenella antigens recognized by monoclonal antibodies are identified by SDS polyacrylamide gel electrophoresis (PAGE) followed by a nitrocellulose blotting procedure [Towbin et al., Proced. Natl. Acad. Sci. (USA) 76: 4350–4354 (1979)].

E. tenella sporozoites and merozoites are lysed and extracted with 1% Nonidet P-40 (Bethesda Research Laboratory) in 10 mM tris buffer (pH 7.5) containing 155 mM $NH_4Cl$, 1.5 mM $MgAc_2$ with protease inhibitors leupeptin and antipain at 30 μg/ml, 4 mM phenyl methyl sulfonyl fluoride and aprotinin (2 trypsin inhibiting units/ml). The lysis procedure involves an incubation for 30 minutes at 0° C. followed by a centrifugation at 2,500x g for 30 minutes. The pellet is discarded and the solubilized material is then used for gel electrophoresis. SDS polyacrylamide gel electrophoresis of samples reduced with 2-mercaptoethanol is performed in a discontinuous trisglycine system on 7 to 15% polyacrylamide gradient gels.

The SDS PAGE separated proteins are transferred onto a nitrocellulose filter electrophoretically for 45 minutes. The nitrocellulose filter is then reacted with either the ascites fluid (1 to 100 Dilution) or spent culture fluid from hybridomas for 16–18 hours at 4° C. Normal rabbit serum was included at a concentration of 10% in all incubations with antibodies. The bound monoclonal antibody is detected by reacting with an $^{125}I$ labelled rabbit anti-mouse IgG antibody (New England Nuclear). The reaction with the second antibody is usually for three to five hours at room temperature. The unbound second antibody is removed by washing. The nitrocellulose filters are then exposed with Kodak X-ray film XAR-5 or SB-5.

Alternatively, the blots are developed by an ELISA method using horseradish peroxidase coupled rabbit anti-mouse IgG (Miles) and chloronaphthol (Aldrich) and $H_2O_2$ (Baker) as substrates. Molecular weights of the protein antigens are determined relative to molecular weight standards.

The antigens recognized by monoclonal antibody 15.84 are illustrative. Monoclonal antibody 15.84 reacts with a doublet of an approximate molecular weight of 130±20 kd. However, the estimation of molecular weights of proteins of the order of 100 kd is subject to variation depending upon the molecular weight standards employed. In addition to the 130±20 kd species, 15.84 also reacts with a band that has an apparent molecular weight of 300±50 kd. The larger molecular weight band constitutes about 15 to 20% of the antigen and perhaps is either an aggregate or a polymeric form of the 130±20 kd species. A control experiment with a monoclonal antibody that is known not to react with protein antigens is used to prove the specificity of the anti-merozoite antibodies. In addition, other controls demonstrate that the monoclonal antibodies are parasite specific and do not react with the host-specific protein.

A summary of molecular weight data of antigens recognized by various antibodies is presented in Table IV. The significant feature is the presence of immunogenic antigens of either molecular weight ≦20 kd or >100 kd. range in E. tenella merozoites.

TABLE IV

SUMMARY OF MOLECULAR WEIGHT DATA

| Anti-Merozoite Monoclonal Antibody | Approximate Molecular Weight of Antigen |
|---|---|
| M1 (1.90) | 300 ± 50 kd. |
| M2 (4.76) | |
| M6 (10.84) | |
| | 130 ± 20 kd. |
| M8 (15.84) | |
| M3 (2.03) | |
| M4 (13.90) | |
| | 18 ± 3 kd. |
| M5 (10.08) | |
| M7 (8.03) | |

Monoclonal antibody 15.84 is considered a neutralizing antibody, and the antigen recognized is considered a protective antigen. In addition the 15.84 antibody is cross-reactive with merozoites and sporozoites of E. tenella as well as sporozoites isolated from E. maxima, E. necatrix, E. acervulina and E. brunetti.

The new monoclonal antibodies, 1.90, 15.84, 13.90, 10.84, 8.03 and 2.03, isolated as described hereinabove, have been deposited with the American Type Culture Collection (ATTC) located in Rockville, Md. and have been added to its permanent collection, No. 1.90 has been assigned the No. HB8336. No. 15.84 has the No. HB 8335. No. 13.90 has been assigned HB8337. No.

10.84 has the No. HB8387. No. 8.03 has been assigned the No. HB8388, and No. 2.03 has the No. HB8389. Access to the antibodies are available during the pendency of the present application to one determined by the Commissioner of Patents and Trademarks to be entitled thereto under 37 C.F.R. 1.14 and 35 U.S.C. 122, and all restrictions on the availability to the public of HB8333, HB8336, HB8337, HB8387, HB8388, and HB8389 will be irrevocably removed upon the granting of a patent on the present application.

What is claimed is:

1. An antigenic, immunogenic, proteinaceous vaccine for combatting Eimeria spp. infection in avians which comprises: an effective amount of *Eimeria tenella* merozoite antigen of 250–350 kd molecular weight which is reactive with anti-merozoite monoclonal antibodies secreted by hybridoma clone 1.90 (ATCC No. HB8336); and a pharmaceutically-acceptable carrier therefore; wherein said antigen is soluble in a detergent containing buffer.

2. A vaccine according to claim 1 additionally containing a stabilizer or pharmaceutically acceptable adjuvant therefore.

3. An antigenic, immunogenic, proteinaceous vaccine for combatting Eimeria spp. infection in avians which comprises: an effective amount of *Eimeria tenella* merozoite antigen of 110–150 kd molecular weight which is reactive with anti-merozoite monoclonal antibodies secreted by hybridoma clone 10.84 (ATCC No. HB8387) and 15.84 (ATCC No. HB8335), and a pharmaceutically-acceptable carrier therefore; wherein said antigen is soluble in a detergent containing buffer.

4. A vaccine accoring to claim 3 additionally containing a stabilizer or pharmaceutically acceptable adjuvant therefore.

5. An antigenic, immunogenic, proteinaceous vaccine for combatting Eimeria spp. infection in avians which comprises: an effective amount of *Eimeria tenella* merozoite antigen of 15–21 kd molecular weight which is reactive with anti-merozoite monoclonal antibodies secreted by hybridoma clones 8.03 (ATCC No. HB8388), 2.03 (ATCC No. HB8389) and 13.90 (ATCC No. HB8337); and a pharmaceutically-acceptable carrier therefore; wherein said antigen is soluble in a detergent containing buffer.

6. A vaccine according to claim 5 additionally containing a stabilizer or pharmaceutically acceptable adjuvant therefore.

7. A method of combatting *Eimeria spp.* infection in avians, said method comprising: administering intraperitoneally, orally or intramuscularly into domestic species, one or a combination of antigens reactive with anti-merozoite monoclonal antibodies secreted by hybridoma clone 1.90 (ATCC No. HB8336), 10.84 (ATCC No. HB8374), 15.84 (ATCC No. HB8335), 8.03 (ATCC No. HB8388), 2.03 (ATCC No. HB8389), 13.90 (ATCC No. HB8337) or mixtures thereof.

8. A vaccine according to claim 1 additionally containing a stabilizer and pharmaceutically acceptable adjuvant therefore.

9. A vaccine according to claim 3 additionally containing a stabilizer and pharmaceutically acceptable adjuvant therefore.

10. A vaccine according to claim 5 additionally containing a stabilizer and pharmaceutically acceptable adjuvant therefore.